US00PP17688P2

(12) United States Plant Patent
Hofmann

(10) Patent No.: US PP17,688 P2
(45) Date of Patent: May 1, 2007

(54) **NEW GUINEA *IMPATIENS* PLANT NAMED 'FISUPNIC PURDEEP'**

(50) Latin Name: *Impatiens hawkeri*
Varietal Denomination: Fisupnic Purdeep

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/330,816

(22) Filed: Jan. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—Jondle & Associates, P.C.

(57) ABSTRACT

A new New Guinea *Impatiens* plant particularly distinguished by numerous, medium to large, deep purple flowers, early flowering, intense green foliage with small leaves, and a medium to tall, well-branched plant habit that is round and tight, is disclosed.

1 Drawing Sheet

Genus and species: *Impatiens hawkeri* W. Bull.
Variety denomination: 'Fisupnic Purdeep'.

BACKGROUND OF THE NEW PLANT

The present invention comprises a new and distinct cultivar of New Guinea *Impatiens,* botanically known as *Impatiens* hawkeri W. Bull, and hereinafter referred to by the cultivar name 'Fisupnic Purdeep'. The new cultivar originated from a hybridization made in the year 2002 in Hillscheid, Germany. The female parent was the proprietary New Guinea *Impatiens* plant 'K02-975-1' (unpatented), while the male parent was the proprietary New Guinea *Impatiens* plant 'K02-1094-1' (unpatented). The seeds produced by the hybridization were sown in a greenhouse in Portugal in the late Fall of 2002. A single plant selection was chosen for further evaluation and for asexual propagation in April 2003 in Moncarapacho, Portugal.

The new cultivar was created in 2002 in Hillscheid, Germany and has been asexually reproduced repeatedly by vegetative cuttings and tissue culture in Moncarapacho, Portugal and Hillscheid, Germany over a two-year period. 'Fisupnic Purdeep' has not been observed under all possible environmental conditions. The present invention has been found to retain its distinctive characteristics through successive asexual propagations.

Plant Breeder's Rights for this cultivar were applied for in Switzerland on Mar. 30, 2005 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Deep purple flower color;
2. Numerous medium to large flowers well above the foliage;
3. Uniform, intense green foliage with small leaves;

4. A medium to tall, round, tight and well-branched plant habit; and
5. An early flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13-weeks old, grown in a greenhouse in Hillscheid, Germany, in May 2005.

DESCRIPTION OF THE NEW CULTIVAR

The following detailed descriptions set forth the distinctive characteristics of 'Fisupnic Purdeep'. The data which define these characteristics were collected from asexual reproductions carried out in Hillscheid, Germany. The plant history was taken on 11- to 12-week old plants which were planted as rooted cuttings in 12-cm pots in late February 2005, and then grown in a greenhouse at a minimum temperature of 16° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K02-975-1' a proprietary lilac flowered New Guinea *Impatiens* plant (unpatented).
*Male parent.*—'K02-1094-1' a proprietary deep bluish-purple flowered New Guinea *Impatiens* plant (unpatented).

Growth:

*Growth and branching habit.*—Medium size, round, bushy, and well-branched; the growth is indeterminate, though weak after the beginning of flowering.

*Height.*—14.7 cm.

*Width.*—24.0 cm.

*Propagation.*—Terminal tips for cuttings.

*Time to produce a finised flowerng plant.*—9 to 10 weeks for a 12-cm pot.

*Time to initiate and develop roots.*—18 days at 22° C.

Branches:

*Average number.*—8.5.

*Length of branches.*—12 cm to 15 cm.

*Internode length.*—3.5 cm to 5.0 cm.

*Diameter of branches.*—0.7 cm to 0.9 cm.

*Stem color.*—RHS 145A (green), at the nodes RHS 185A (reddish-brown).

Leaves:

*Arrangement.*—Primarily in whorls.

*Size.*—Length: 10.8 cm. Width: 4.0 cm.

*Shape.*—Elliptic.

*Margin.*—Slightly serrate, ciliated.

*Apex.*—Acuminate.

*Base.*—Acute.

*Color* (*mature leaves*).—Upper surface: Near RHS 137A or between RHS 137A and RHS 139A (medium-green). Lower surface: RHS 138B (light-green).

*Color* (*immature leaves*).—Upper surface: Between RHS 137D and RHS 143A. Lower surface: RHS 138B (light-green).

*Texture.*—Glabrous, somewhat glossy, faintly rugose or rippled.

*Venation color.*—Upper surface: RHS 50B (pink), at the base. Lower surface: RHS 143C (light-green).

*Variegation.*—None.

*Petioles.*—Length: 2.5 cm. Diameter: 0.3 cm to 0.4 cm. Color: Upper surface: RHS 180A. Lower surface: RHS 185A. Texture: Glabrous.

Flower buds:

*Shape.*—Ovoid.

*Size.*—Length: 2.3 cm. Diameter: 1.6 cm.

*Color.*—RHS 61A.

Inflorescence:

*Blooming habit.*—9 weeks after planting of rooted cuttings.

*Inflorescence type.*—Flowers appear solitary in the leaf axils of the upper nodes of the stems.

*Number of flowers per node.*—6 to 8, in various stages of development Flowering season: Indeterminate, mainly from March to October, depending on light intensity.

*Lastingness of individual blooms.*—Up to 14 days (in a greenhouse at 18° C.).

*Fragrance.*—None.

*Peduncle.*—Color: RHS 180A (brownish-red). Size: Length: 4.5 cm. Diameter: 0.1 cm. Texture: Glabrous, flexible.

Flowers:

*Form of corolla.*—Single-type, 5 petals.

*Shape of corolla.*—Zygomorphic, butterfly-shaped.

*Corolla size.*—Length: 7.4 cm. Width: 7.3 cm. Depth: 1.5 cm.

Petals:

*Shape.*—Cordate, moderately lobed at the top end.

*Apex.*—Emarginate, top petal slightly cupped.

*Base.*—Attenuate.

*Margin.*—Entire.

*Petal size.*—Top: Length: 3.0 cm. Width: 4.6 cm. Lateral: Length: 3.4 cm. Width: 4.0 cm. Lower: Length: 3.6 cm. Width: 4.2 cm.

*Color.*—General color description: Bluish-purple, no markings, but a little variable. Upper surface: Deeper than RHS N74A, but becoming deeper, RHS 71A, or more bluish with maturing, towards RHS N80A. Lower surface: RHS 71C. Eye Zone: No distinct eye zone.

*Petal texture.*—Smooth.

*Aspect.*—Flat, banner petal may be slightly cupped.

Spur:

*Shape.*—Downwardly curved.

*Color.*—RHS 53C (red-purple).

*Size.*—Length: 5.5 cm to 6.0 cm. Diameter: 0.3 cm (at the flower end).

Reproductive organs:

*Stamens.*—Number: 5 fused. Stamen color (upper surface color): RHS N66B (red-purple). Anthers: Fused, hooded. Pollen color: RHS 8D (whitish-yellow).

*Pistils.*—Style and stigma: 5, very short, RHS 150D (pale-yellow). Ovary: 5-celled. Ovary length: 0.5 cm. Ovary color: RHS 143A (surface green), later RHS 147A.

Fruit and seed set: No seed set observed.

Disease and insect resistance: No particular resistance or susceptibility has been observed.

COMPARISON WITH PARENTAL AND COMMERCIAL CULTIVARS

'Fisupnic Purdeep' differs from the female parent 'K02-975-1' (unpatented) by having deeper and more red-purple flowers and a more intense green foliage color while 'K02-975-1' has lilac flowers and medium green foliage.

'Fisupnic Purdeep' differs from the male parent 'K02-1094-1' (unpatented), by having a more reddish hue of flower color than 'K02-1094-1'.

'Fisupnic Purdeep' differs from the commercial cultivar 'Fisimp 284' (U.S. Plant Pat. No. 13,694) by having a deeper purple flower color, more butterfly-shaped, but less cup-shaped flowers, and a taller plant habit than 'Fisimp 284'.

'Fisupnic Purdeep' differs from cultivar 'Fisupnic Burgy' (U.S. Plant Pat. No. 16,032) by having shorter leaves and a deeper and more bluish overall flower color than 'Fisupnic Burgy'.

I claim:

1. A new and distinct cultivar of New Guinea *Impatiens* plant as shown and described herein.

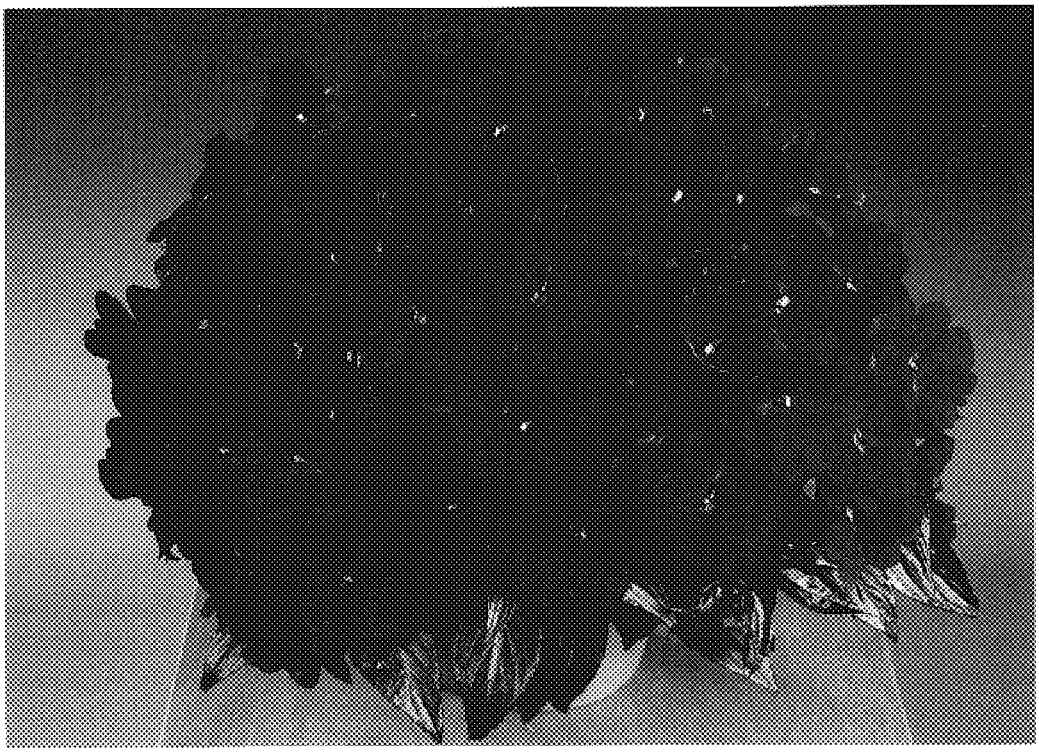

* * * * *